United States Patent
Popa et al.

(10) Patent No.: US 9,610,173 B2
(45) Date of Patent: Apr. 4, 2017

(54) VERTEBRAL BODY REPLACEMENT APPARATUS

(71) Applicant: DePuy Synthes Products, Inc, Raynham, MA (US)

(72) Inventors: Samantha Popa, Columbus, OH (US); Roman Randegger, Aarburg (CH); Tom Overes, Langendorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 428 days.

(21) Appl. No.: 13/929,521

(22) Filed: Jun. 27, 2013

(65) Prior Publication Data

US 2015/0005880 A1 Jan. 1, 2015

(51) Int. Cl.
*A61F 2/44* (2006.01)
*A61F 2/30* (2006.01)
*A61F 2/28* (2006.01)

(52) U.S. Cl.
CPC ............... *A61F 2/446* (2013.01); *A61F 2/44* (2013.01); *A61F 2/442* (2013.01); *A61F 2/30744* (2013.01); *A61F 2/30767* (2013.01);
(Continued)

(58) Field of Classification Search
CPC .................................. A61F 2/44–2/447; A61F 2002/4415–2002/4495
USPC ............................................ 623/17.11–17.16
See application file for complete search history.

(56) References Cited

U.S. PATENT DOCUMENTS

| 6,395,035 B2 | 5/2002 | Bresina et al. |
| 6,524,341 B2 | 2/2003 | Lang et al. |
(Continued)

FOREIGN PATENT DOCUMENTS

| EP | 1 459 710 | 9/2004 |
| WO | 2005/039454 | 5/2005 |
| WO | 2008/106912 | 9/2008 |

OTHER PUBLICATIONS

International Search Report and Written Opinion (PCT/US2014/041830); Sep. 25, 2014.

*Primary Examiner* — Nicholas Plionis
(74) *Attorney, Agent, or Firm* — Dunlap Codding, P.C.

(57) ABSTRACT

A vertebral body replacement apparatus includes an outer body member having a first end, a second end, and an opening, and an inner body member having a first end, a second end, and an inner surface defining an opening. The first end of the inner body member is received in the opening of the outer body member such that the inner body member and the outer body member are movable relative to one another. A support member has a first end secured within the inner body member and a second end extending a distance beyond the inner body member. The second end of the support member deflects relative to the first end of the outer body member in response to a force applied thereto and returns to a substantially non-deflected condition upon release of the force.

24 Claims, 6 Drawing Sheets

(52) U.S. Cl.
CPC ... *A61F 2/30965* (2013.01); *A61F 2002/2835* (2013.01); *A61F 2002/30006* (2013.01); *A61F 2002/3055* (2013.01); *A61F 2002/30062* (2013.01); *A61F 2002/3098* (2013.01); *A61F 2002/30235* (2013.01); *A61F 2002/30405* (2013.01); *A61F 2002/30433* (2013.01); *A61F 2002/30471* (2013.01); *A61F 2002/30476* (2013.01); *A61F 2002/30495* (2013.01); *A61F 2002/30497* (2013.01); *A61F 2002/30563* (2013.01); *A61F 2002/30566* (2013.01); *A61F 2002/30571* (2013.01); *A61F 2002/30578* (2013.01); *A61F 2002/30594* (2013.01); *A61F 2002/30601* (2013.01); *A61F 2002/30616* (2013.01); *A61F 2002/30784* (2013.01); *A61F 2002/30841* (2013.01); *A61F 2002/30878* (2013.01); *A61F 2002/30925* (2013.01); *A61F 2002/30957* (2013.01); *A61F 2002/30985* (2013.01); *A61F 2002/4475* (2013.01); *A61F 2310/00011* (2013.01); *A61F 2310/00017* (2013.01); *A61F 2310/00023* (2013.01); *A61F 2310/00029* (2013.01); *A61F 2310/00359* (2013.01); *A61F 2310/00407* (2013.01); *A61F 2310/00461* (2013.01); *A61F 2310/00796* (2013.01)

(56) References Cited

U.S. PATENT DOCUMENTS

| | | | |
|---|---|---|---|
| 8,152,851 B2 | 4/2012 | Mueller et al. | |
| 8,252,059 B2 | 8/2012 | Overes et al. | |
| 8,328,871 B2 | 12/2012 | Capote et al. | |
| 2004/0073314 A1 | 4/2004 | White et al. | |
| 2007/0179610 A1* | 8/2007 | Biedermann | A61F 2/44 623/16.11 |
| 2010/0016969 A1* | 1/2010 | Richter | A61F 2/442 623/17.11 |
| 2010/0152856 A1 | 6/2010 | Overes et al. | |
| 2011/0251692 A1* | 10/2011 | McLaughlin | A61F 2/44 623/17.16 |
| 2012/0029640 A1* | 2/2012 | Capote | A61F 2/44 623/17.16 |
| 2012/0101576 A1* | 4/2012 | Dewey | A61F 2/44 623/17.11 |
| 2014/0135931 A1 | 5/2014 | Popa et al. | |

* cited by examiner

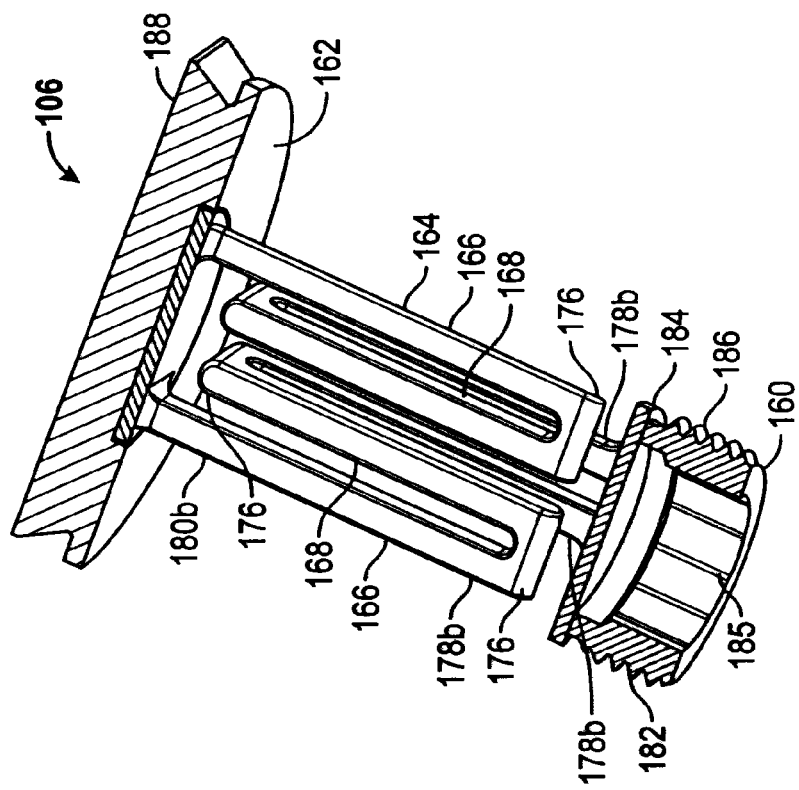
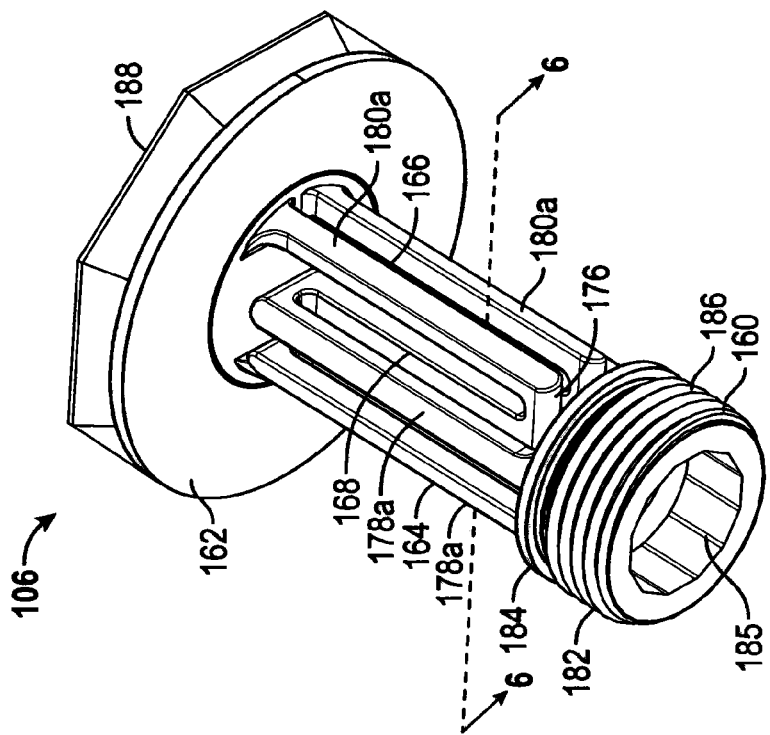
FIG. 6
FIG. 5

VERTEBRAL BODY REPLACEMENT APPARATUS

BACKGROUND

1. Field of the Inventive Concepts

The inventive concepts disclosed herein are generally directed to medical implants, and more particularly, but not by way of limitation, to a vertebral body replacement apparatus configured to be at least partially dynamic when implanted into a spine.

2. Brief Description of Related Art

The human spinal column, or spine, is highly complex, in that it includes over twenty bones coupled to one another so as to support the body and to house and protect critical elements of the nervous system. In addition, the spine is a highly flexible structure, capable of a high-degree of curvature and twist in multiple directions. The bones and connective tissues of an adult human spine are coupled sequentially to one another by a tri-joint complex which consists of an anterior joint between vertebral bodies, and two posterior facet joints. The vertebral bodies of adjacent vertebrae are separated and cushioned by cartilage spacers referred to as intervertebral discs. The vertebral bones of the spine are classified as cervical, thoracic, lumbar, and sacral. The cervical portion of the spine, which includes the upper portion of the spine up to the base of the skull, is the most flexible of all the regions of the spinal column, and includes the first seven vertebrae. The twelve intermediate bones comprise the thoracic vertebrae, and connect to the lower spine which comprises the five lumbar vertebrae. The base of the spine includes the sacral bones (including the coccyx).

A typical human vertebra consists of two essential parts: an anterior (front) segment, which is the vertebral body; and a posterior (back) segment—the vertebral (neural) arch—which encloses the vertebral foramen. The vertebral arch is formed by a pair of pedicles and a pair of laminae, and supports seven processes—four articular, two transverse, and one spinous.

The vertebral body is the largest portion of the vertebrae and is generally cylindrical in shape. Vertebral bodies have upper and lower surfaces, which are generally flat or slightly concave. The surfaces are roughened to allow for the attachment of the intervertebral discs. The vertebral bodies and the intervertebral disks cooperate to provide structural support to the spinal column, with the intervertebral disks cushioning the vertebrae and absorbing and adapting to forces exerted on the vertebral bodies.

In some cases of spinal injuries, the forces exerted on the spinal column are so great, as to cause a partial or complete fracture or collapse of one or more of the vertebral bodies, and significant damage to the intervertebral disks surrounding the fractured or collapsed vertebral body. A vertebral body fracture or collapse may also be caused by osteoporosis, arthritis, tumors, or other diseases.

Regardless of the cause, it is difficult for the damaged vertebral body and intervertebral disks to heal due to the constant forces exerted on the spinal column, and/or due to disease progression. Further, due to bulging or displaced damaged vertebral body fragments or intervertebral disks, pressure may be exerted on the spinal cord, or other neural tissues surrounding the damaged vertebral body or intervertebral disks, which may lead to significant pain, neurological damage, and even paralysis in some severe cases.

A surgical procedure called vertebral body replacement (VBR) has been developed to remove the damaged vertebral body and intervertebral disks, and to replace them with an implantable VBR apparatus, such that the proper height, alignment, and curvature of the patient's spinal column are maintained or are not significantly compromised.

VBR is generally performed by locating the damaged vertebral body (e.g., with medical imaging) and accessing it via an appropriate surgical incision. Once the vertebral body is accessed, surgical tools may be used to remove the damaged portion or the majority of the vertebral body and the two intervertebral disks surrounding the damaged vertebral body, such that the lower surface of the vertebral body above and the upper surface of the vertebral body below the removed vertebral body are exposed.

Next, a generally cylindrical VBR apparatus of appropriate size is selected and inserted in the location of the removed vertebral body. The VBR apparatus generally has endplates which contact the exposed lower surface of the vertebral body above the removed vertebral body, and the exposed upper surface of the vertebral body below the removed vertebral body. The endplates are configured to engage the VBR apparatus with the two adjacent vertebral bodies and to keep it in place once implanted. The design, shape, and angle of the endplates that contact the adjacent vertebrae are selected to ensure proper spinal height, alignment, and curvature, and to securely attach the VBR apparatus to adjacent vertebrae, such that the VBR apparatus does not become dislodged, or otherwise displaced post-implantation.

Some existing VBR apparatuses allow surgeons to adjust the height of the VBR apparatus to match the original height, alignment, or curvature of the patient's spine, and some VBR apparatuses have a porous hollow body or cage, which allows surgeons to insert a bone graft into the VBR apparatus. The bone graft may eventually grow through, or around, the VBR apparatus, and may fuse the two vertebrae that are in contact with the VBR apparatus over time.

In some cases, one or more supplemental fixation devices, such as stabilizing rods, plates, or bone screws, may be attached to the vertebrae above and below the VBR apparatus and/or to the VBR apparatus to absorb some of the forces exerted on the VBR apparatus and/or to provide additional stabilization of the spine while the bone graft is fusing the two vertebrae together. If the VBR apparatus is a bone-fusion device, over the next several months the bone graft grows into, or around, the VBR apparatus to eventually fuse the adjacent vertebral bodies together. If the VBR apparatus is a non-fusion device, the supplemental fixation devices and the VBR apparatus may function to replace the removed vertebral body and the VBR apparatus and adjacent vertebrae may not be fused together.

However, existing VBR apparatuses suffer from several disadvantages. For example, existing VBR apparatuses are generally rigid and inelastic devices and have bone-contacting surface designs which, due to local patient anatomies and angulation, may result in concentrating a large amount of force onto a small area on the prior art VBR apparatus bone-contacting surfaces. This is referred to as point-loading and may increase the chances of adjacent vertebral body subsidence and VBR apparatus failure.

Further, rigid existing VBR apparatuses remain static (e.g., inelastic in an axial and/or lateral direction) once implanted and transfer strain away from the graft inside the VBR apparatus and onto adjacent vertebral bodies contacted by existing VBR apparatuses. Bone remodeling is controlled by peak strain, and when a bone is subjected to just a few cycles per day of strain above a certain level, the bone is maintained and/or new bone formation occurs the strengthen the bone. In the case of fusion VBR apparatuses, it would be advantageous to provide a substantially elastic VBR apparatus that transfers some strain and/or other forces to the graft material to stimulate the graft to fuse the adjacent vertebra more quickly than prior art implants.

Some attempts have been made in the prior art to include some elasticity in the endplates of VBR apparatuses, such as the endplates described in PCT patent application Ser. No. PCT/US2012/65287, filed on Nov. 15, 2012, and in U.S. Pat. No. 8,252,059, the entire disclosures of which are expressly incorporated herein by reference. However, such elasticity has been limited to the endplates or to disk-replacement devices, while existing VBR apparatuses have remained inelastic and static.

Accordingly, a need exists in the prior art for a VBR apparatus configured to remain at least partially dynamic in a lateral and/or axial direction when implanted into a spine, to more efficiently distribute and absorb forces applied to the VBR apparatus and to stimulate bone graft growth. It is to such VBR apparatuses that the inventive concepts disclosed herein are directed.

BRIEF DESCRIPTION OF THE DRAWINGS

FIG. 5 is a perspective view of an exemplary embodiment of the support member.

FIG. 6 is a cross-sectional view taken along line 6-6 of FIG. 5.

DETAILED DESCRIPTION OF EXEMPLARY EMBODIMENTS

Figure 2:
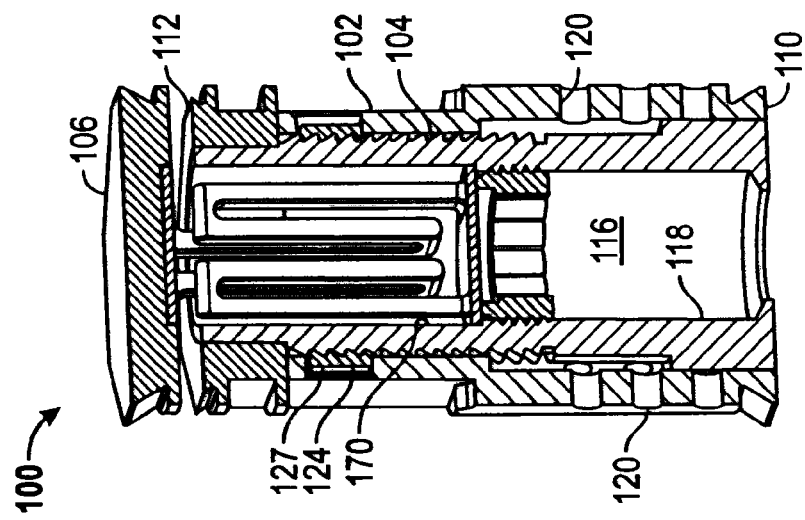
FIG. 2 is a cross-sectional view taken along line 2-2 of FIG. 1.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments, or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having," and any variations thereof, are intended to cover a non-exclusive inclusion. For example, a process, method, article, or apparatus that comprises a list of elements is not necessarily limited to only those elements, and may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments disclosed herein. This is done merely for convenience and to give a general sense of the inventive concepts. This description should be read to include one or at least one and the singular also includes the plural unless it is obvious that it is meant otherwise.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

As is known by persons of ordinary skill in the art, established human anatomical orientation designations are used to avoid ambiguities when referring to a body part relative to another body part. A standard anatomical position (i.e., standing upright facing forward with arms to the side, palms facing forward, thumbs pointing laterally away from the body) has been established, and such orientation designations refer to the various body parts in the standard position, without regard to their actual position. For the purposes of the instant disclosure, such standard human anatomy terminology may be used to describe the various orientation and interrelationships of the different parts of a user's body. For example, the terms "anterior," "posterior," "superior," "inferior," "lateral," "medial" and related terms or phrases may be used to designate relative positions and orientations in the patient's body to which reference is made, and are not meant to be limiting. Further, the terms "left," "right," "lower," "upper," "top," and "bottom" may designate general directions in the drawings to which reference is made, for example, and are not meant to be limiting. The terms "inner," "inwardly," or "distally," and "outer," "outwardly," or "proximally" may refer to directions toward or away from the geometric center of a device and related parts thereof, or a patient's body, for example, and are not intended to be limiting.

As used herein, the term "patient" is not limited to a human being, and is intended to include all organisms, whether alive or dead, including any species having soft tissues and bones. For example, VBR apparatuses according to the instant disclosure may be used in a living human, horse, cow, sheep, cat, dog, and the like. As another example, VBR apparatuses according to the instant disclosure may be used in a non-living organism, or in an artificial anatomical model to train medical or veterinary personnel in surgical techniques. Further, a virtual representation of a VBR apparatus according to the instant disclosure may be used in a virtual simulation to train medical or veterinary personnel in surgical techniques, for example.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 1:
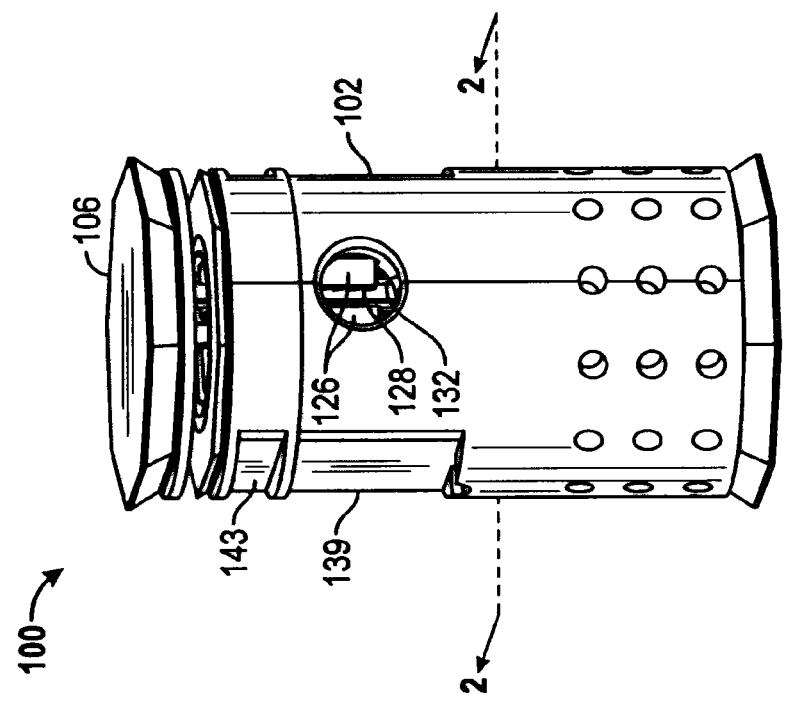
FIG. 1 is a perspective view of an exemplary embodiment of a VBR apparatus according to the inventive concepts disclosed herein.

Referring now to drawings, and more particularly to FIGS. 1-2, an exemplary embodiment of a VBR apparatus 100 is shown. The VBR apparatus 100 includes an outer body member 102, an inner body member 104, and a support member 106. The inner body member 104 may be received in the outer body member 102 such that the inner body member 104 and the outer body member 102 are movable relative to one another in a telescoping relationship as will be described below.

Figure 3:
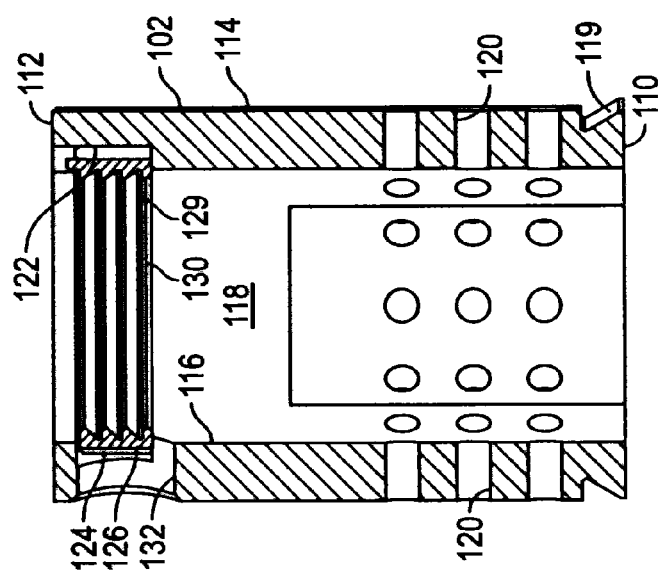
FIG. 3 is a cross-sectional view of an outer body member of the VBR apparatus of FIG. 1.

Referring now to FIGS. 2-3, the outer body member 102 includes a sidewall 108, a first end 110, a second end 112, an external surface 114, and an internal surface 116 defining an axial opening 118. The outer body member 102 can be constructed of any desired implantable material, such as polyether-ether-ketone (PEEK), PEEK with titanium coating, porous titanium, polymers (e.g., silicone), cobalt-chromium (CoCr) alloys, or combinations thereof, for example.

One or more transverse openings 120 may be formed in the sidewall 108 and may extend from the external surface 114 through the internal surface 116 so as to intersect with the axial opening 118, for example. The transverse openings 120 are configured to allow a bone graft provided in the axial opening 118 to grow therein. Any desired number of transverse openings 120 may be implemented with exemplary embodiments, while in some embodiments the transverse openings 120 may be omitted. The transverse openings 120 may have any desired size, shape, and orientation, and may extend at any angle, such as an angle of about 90° to the longitudinal axis of the VBR apparatus 100.

An annular notch 122 is formed in the internal surface 116 of the sidewall 108 so as to intersect with the axial opening 118. The annular notch 122 is configured to at least partially receive a locking member 124 therein.

The locking member 124 is a substantially C-shaped open ring and has ends 126 (FIG. 1) separated by a gap 128 (FIG. 1), an outer surface 127 (FIG. 2) configured to be at least partially received in the annular notch 122, and an inner surface 129 having one or more ratcheting teeth 130 (FIG. 3) formed therein. The locking member 124 may have a diameter smaller than a diameter of the annular notch 122, so that the locking member 124 may be selectively moved between an expanded position to allow the outer body member 102 and the inner body member 104 to ratchet or otherwise move relative to one another in an axial direction, and a locked position to secure the inner body member 104 and the outer body member 102 relative to one another. In some exemplary embodiments, the ratcheting teeth 130 are directional, so that the outer body member 102 and the inner body member 104 are movable away from one another in axial direction so as to increase the height of the VBR apparatus 100, while at the same time are prevented from moving in the opposite direction so as to maintain the desired height of the VBR apparatus 100.

A lock opening 132 may be formed in the sidewall 108 so as to intersect with the axial opening 118 and so as to open at the annular notch 122. The lock opening 132 is configured so that the gap 128 of the locking member 124 is visible and/or accessible through the lock opening 132, to allow a user to visually and/or physically verify that the locking member 124 is in the locked position, and to allow the user to insert a suitable tool into the gap 128 via the lock opening 132 to force the locking member 124 into its expanded position and allow the outer body member 102 and the inner body member 104 to move relative to one another in an axial direction to decrease the height of the VBR apparatus 100. In some embodiments, the locking member 124 may be omitted and any desired mechanism may be implemented to secure the outer body member 102 and the inner body member 104 to one another, such as threads, set screws, brackets, welds, adhesives, and combinations thereof, for example.

The second end 112 may also include a surface 134 configured to allow a collar of the inner body member 104 to rest thereon when the VBR apparatus 100 is substantially in the collapsed position as will be described below.

The first end 110 may include a flange 136 formed therein. The flange 136 is configured to be matingly inserted into a corresponding notch of an endplate configured to engage a vertebral body such as the endplate described with reference to FIG. 10 below. The flange 136 is shown as being substantially octagonal in shape, but it is to be understood that the flange 136 may have any desired shape configured to correspond to a shape of any desired endplate.

A grasping notch 139 (FIG. 1) may be formed in the sidewall 108 to allow a surgical tool to grasp the outer body member 102 as described with reference to FIG. 11 below.

Figure 4:
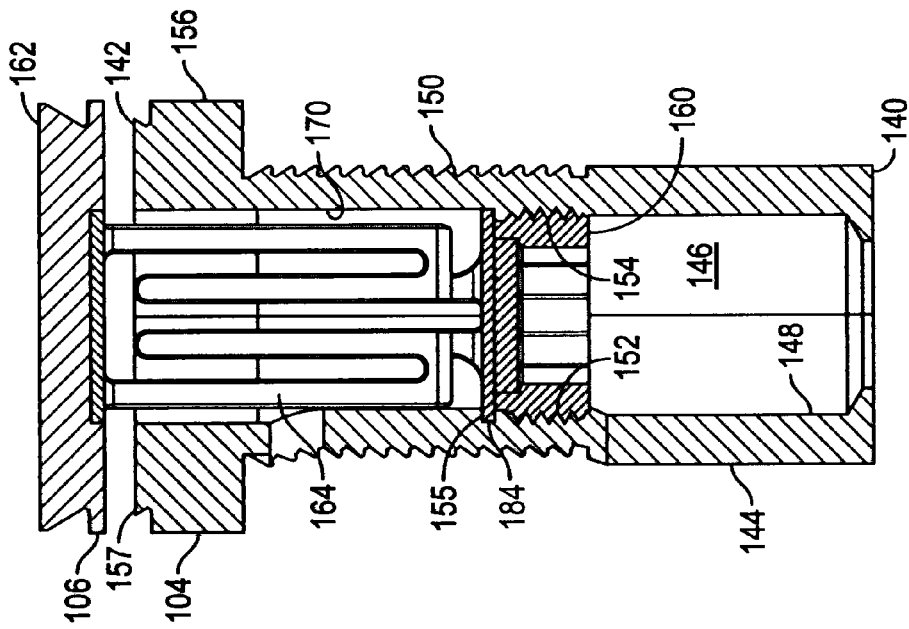
FIG. 4 is a cross-sectional view of an inner body member and a support member of the VBR apparatus of FIG. 1.

Referring now to FIG. 4, the inner body member 104 has a sidewall 138 with a first end 140 and a second end 142, and an outer surface 144 and an inner surface 146 defining an axial opening 148 extending substantially from the first end 140 to the second end 142.

The first end 140 of the inner body member 104 is shaped and sized such that the first end 140 can be at least partially inserted into the axial opening 118 of the second end 112 of the outer body member 102, so that the outer surface 144 of the sidewall 138 is positioned into the axial opening 118, and so that the first end 140 of the inner body member 104 is received in the axial opening 118 of the outer body member 102 such that the inner body member 104 and the outer body member 102 are movable relative to one another in a telescoping relationship such that the distance between the first end 110 of the outer body member 102 and the second end 142 of the inner body member 104 is selectively adjustable.

The second end 142 may include a collar 156 configured to rest against the surface 134 when the VBR apparatus 100 is in the collapsed position. The collar 156 may include a grasping notch 143 (FIG. 1) configured to allow a suitable surgical tool to grasp the collar 156.

The outer surface 144 may include one or more serrations 150 formed therein and at least partially extending along the outer surface 144. The serrations 150 extend along the outer surface 144 such that the serrations 150 are positioned over the annular notch 122 as the inner body member 104 is inserted into the axial opening 118 of the outer body member 102. The serrations 150 are configured to matingly engage, interlock, mesh, or otherwise connect with the ratcheting teeth 130 of the locking member 124. The serrations 150 can be implemented as directional teeth in some exemplary embodiments.

The sidewall 138 further includes a seat 152 formed in the inner surface 146 thereof. The seat 152 may include one or more columns of threads 154 formed in the inner surface 146 of the sidewall 138, and may be configured so that the support member 106 is threadingly attached to the inner body member 104 via the seat 152. The seat 152 may also include a shoulder 155 configured to engage a flange of the support member 106 therein as will be described below. It is to be understood that in some exemplary embodiments the support member 106 and the inner body member 104 may be formed as a unitary component.

Referring to FIGS. 4-6, the support member 106 includes a first end 160 configured to be inserted into the axial opening 148 of the inner body member 104 and to be secured to the inner body member 104, and a second end 162 configured to extend at a distance beyond the second end 142 of the inner body member 104 and to receive an endplate configured to engage a vertebral body, such as the endplate described with reference to FIG. 10 below. At least a portion of the support member 106 may be resilient, and the first end 160 of the support member 106 may be supported by the inner body member 104 in a way so that the second end 162 of the support member 106 deflects relative to the first end 110 of the outer body member 102 in response to a force applied to the second end 162 of the support member 106, and returns to a substantially non-deflected condition upon release of the force. The support member 106 may include a spring portion 164 positioned between the first end 160 and the second end 162 of the support member 106.

The first end 160 and the second end 162 can be manufactured from any biocompatible material including but not limited to nitinol or other memory metals, high flexible metals, plastics, reinforced plastics, resilient materials, and combinations thereof. For example, depending on the required flexibility and endurance requirements, the support member 106 can be manufactured from stainless steel, cobalt chromium, nitinol, or plastics, and combinations thereof. The support member 106 can also be manufactured via and suitable techniques, such as injection molding or 3D printing. In some exemplary embodiments, the first end 160 and the second end 162 can be manufactured from titanium or a titanium alloy for its osseo-conductive characteristics.

The spring portion 164 may include one or more struts 166, and one or more hanging beams 168 and may be separated from the inner surface 146 of the sidewall 138 by a gap 170 (FIG. 4) when the support member 106 is in the non-deflected condition, which allows the spring portion 164 to be resilient or to move or deflect axially and/or laterally and/or rotationally in the gap 170 relative to the second end 142 of the inner body member 104 when a force is applied to the first end 160 of the support member 106, and to return to a substantially non-deflected condition upon release of the force. The movement or deflection of the spring portion 164 of the support member 106 limited by the size (e.g., width) of the gap 170 such that when the spring portion 164 comes into contact with the inner surface 146 of the sidewall 138 further lateral movement or deflection of the support member 106 is limited or substantially prevented.

The struts 166 generally extend vertically from a first surface 172 (e.g., in a substantially perpendicular direction relative to the first surface 172) of the first end 160 and vertically from a second surface 174 of the second end 162. The struts 166 include one or more horizontal curved portions 176. The curved portions 176 provide interconnection between the struts 166 extending from the first end 160, and a first end of the one or more hanging beams 168, and an interconnection between the struts 166 extending from the second end 162 to a second end of the one or more hanging beams 168. This interconnection between the struts 166 and the hanging beams 168 allows the first end 160 and the second end 162 to move, compress, and/or flex with respect to one another.

The spring portion 164 is shown as including two strut pairs 178 (FIG. 5), respectively, which cooperate to define a substantially cylindrical shape. Each strut pair 178 is not interconnected with another strut pairs 178. Instead, each of the struts 166 of the strut pairs 178 connected with the first end 160 and with the second end 162 includes a respective curved portion 176 which connect that strut 166 to a respective hanging beam 168. Because each strut 166 or each strut pair 178 (two strut pairs 178 and four struts 166 in total in this example are connected with the first end 160 and the second end 162) includes a curved portion 176 that connects it to a separate hanging beam 168, this exemplary embodiment includes four hanging beams 168.

In the exemplary embodiment shown in FIGS. 5-6, a total of eight struts 166 are connected with four hanging beams 168 via eight curved portions 176 to connect the first surface 172 of the first end 160 and the second surface 174 of the second end 162 to one another. More specifically, for example, a first curved portion 176, which is connected at one end to one of the struts 166 of the first end 160, extends horizontally towards an interior of the support member 106 and is connected at an opposite end to a first end of one of the hanging beams 168. Similarly, for example, a second curved portion 176, which is connected at one end to one of the struts 166 of the second end 162, extends horizontally towards the interior of the support member 106 and is connected at an opposite end to a second end of the hanging beam 168. The struts 166 and/or the strut pairs 178 are separated from the inner surface 146 of the sidewall 138 by the gap 170, so that the struts 166 and/or strut pairs 178 may bend or flex in a lateral direction by moving or laterally deflecting in the gap 170, for example. In some exemplary embodiments the struts 166 and/or strut pairs 178 may deflect so as to partially span the gap 170, while in some exemplary embodiments the struts 166 and/or strut pairs 178 may deflect so as to come into contact with the inner surface 146 of the sidewall 138 when axial and/or lateral forces are applied to the first end 160 of the support member 106. Further deflection of the support member 106 may be limited or substantially prevented by the sidewall 138 once the struts 166 come into contact with the inner surface 146.

It is contemplated that the spring portion 164 of the support member 106 according to the inventive concepts disclosed herein may include any desired number of struts 166, curved portions 176, and hanging beams 168, as may be deemed necessary to achieve particular design and performance criteria. As will be generally appreciated by one of ordinary skill in the art, the number of struts 166, the number of curved portions 176, the number of hanging beams 168, length, size, and cross-sectional shape of the struts 166, curved portions 176, and hanging beams 168, the selected material for the spring portion 164 of the support member 106, etc., can be varied to tailor the flexibility and/or degree of axial and/or lateral deflection characteristics for the VBR apparatus 100, along with varying the size of the gap 170 as desired.

The gap 170 may be substantially annular or may have any other desired shape, and may have any desired size depending on the desired degree of deflection for the VBR apparatus 100. The degree or amount of deflection of the support member 106 in an axial and/or lateral direction and/or rotationally is adjustable by adjusting the size of the gap 170 and/or the length of the struts 166, as will be appreciated by persons of ordinary skill in the art having the benefit of the instant disclosure. For example, to increase the degree of flexibility or deflection of the support member 106, the size of the gap 170 may be increased and/or the height of the second end 162 of the support member 106 may be increased (e.g., by increasing the length of the struts 166). To decrease the degree of flexibility of the support member 106, one or more of the above parameters may be decreased. This configuration allows the spring portion 164 of the support member 106 to be resilient or to move laterally, axially and/or rotationally relative to the inner body member 104, and the first end 160 to move laterally, axially and/or rotationally relative to the first end 110 of the outer body member 102.

The spring portion 164 and/or the struts 166, the curved portions 176, and the hanging beams 168 can be manufactured from CoCr or other elastic or super elastic metal for its relevant material/fatigue properties and biocompatible character. Other material combinations are also possible with the inventive concepts disclosed herein. The struts 166 are coupled to the first surface 172 of the first end 160 and the second surface 174 of the second end 162 by any desired mechanism including but not limited to via welding, tacking, adhesive, hinges, a fixation device (e.g., screws or rivets), or any other means of fixation now known or hereafter developed. Alternatively, the support member 106 can be manufactured as a single, integral piece, for example.

In some exemplary embodiments, the spring portion 164 of the support member 106 may be implemented and may function substantially similarly to the flexible elements described in U.S. Pat. No. 8,252,059, the entire disclosure of which is hereby expressly incorporated herein by reference, while in some embodiments the support member 106 may be implemented as any desired spring member connected with a body of a VBR apparatus and separated by a gap therefrom, and configured to be axially and/or laterally and/or rotationally deflectable relative to the inner body member 104 with such deflection being limited by the size of the gap 170 separating the support member 106 and the inner body member 104.

The first end 160 may include a connector 180. The connector 180 may be associated with the first end 160 in any desired manner and may include a threaded portion 182, a flange 184, and an axial driver opening 185 formed therein. The threaded portion 182 may be substantially cylindrical and includes threads 186 configured to threadingly interlock with the columns of threads 154 of the seat 152, so that the first end 160 is detachably connectable to the inner body member 104. The flange 184 may be configured to engage the shoulder 155 of the seat 152 in a manner that the shoulder 155 functions as a stop. A suitable surgical drive, such as a hexagonal drive, or any other desired shape drive, may be inserted into the driver opening 185 and used to impart rotational motion on the support member 106 so as to threadingly connect the threaded portion 182 with the seat 152 and so as to engage the flange 184 with the shoulder 155, for example. It is to be understood that the connector 180 may be connected with the seat 152 in any desired manner, such as by being press-fitted, welded, glued, joined, or otherwise connected therewith. Further, in some exemplary embodiments, the support member 106 and the inner body member 104 may be connected to one another in any desired manner or may be formed as a unitary component.

The second end 162 end may include a flange 188. The flange 188 may be connected to the second end 162 in any desired manner, and in some exemplary embodiments, the flange 188 and the second end 162 may be formed as a unitary component. The flange 188 may be implemented similarly to the flange 136 and is configured to associate an endplate with the second end 162.

One advantage of the configurations of the support member 106 according to the inventive concepts disclosed herein is that the incorporation of the spring portion 164 enables dampening movement, flexing, deflection and/or compression of the support member 106 and specifically of the first end 160 and the second end 162 with respect to one another in an axial direction and/or in a lateral direction and/or rotationally. In addition, incorporation of one or more struts 166 into the spring portion 164, enables at least six degrees of freedom while motion and rotation of the support member 106 is limited thanks to the intrinsic structure and/or length of the struts 166 and by the size of the gap 170 when the support member 106 is associated with the inner body member 104. The spring portion 164 of the support member 106 is configured to be elastic (e.g., by moving or deflecting) in the axial direction and/or in the lateral direction relative to the second end 142 of the inner body member 104 and/or relative to the first end 110 of the outer body member 102, so as to maintain the VBR apparatus 100 substantially elastic in the axial direction and/or in the lateral direction when implanted. The support member 106 may include one or more mechanical stops (not shown) to prevent the support member 106 from over extension in some exemplary embodiments.

In contrast with previous VBR apparatuses, incorporating a spring portion 164 enables the support member 106 to withstand high axial forces while still allowing sufficient flexibility for bending in an axial direction and/or in a lateral direction relative to the second end 142 of the inner body member 104 and/or relative to the first end 110 of the outer body member 102. In addition, because the spring portion 164 of the support member 106 does not contain any articulating surfaces, no abrasion particles will be created during normal use of the support member 106. The support member 106 does not generate material debris because the components of the spring portion 164 of the support member 106 do not touch one another when the support member 106 deflects.

The VBR apparatus 100 may be assembled by inserting the locking member 124 into the annular notch 122 of the outer body member 102, and positioning the locking member 124 so that the ends 126 and the gap 128 are positioned at the lock opening 132. Next, the inner body member 104 may be slidably inserted into the outer body member 102 (e.g., by sliding the first end 140 of the inner body member 104 into the axial opening 118 of the outer body member 102) so that the serrations 150 interlock with the ratcheting teeth 130, so as to selectively adjust the distance between the first end 110 of the outer body member and the second end 142 of the inner body member 104. In some exemplary embodiments, the support member 106 may be connected with the inner body member 104 prior to inserting the inner body member 104 in the outer body member 102, while in some exemplary embodiments the support member 106 may be connected with the inner body member 104 after the inner body member 104 is inserted in the outer body member 102. The support member 106 can be connected with the inner body member 104 by slidably inserting the first end 160 of the support member 106 into the axial opening 148 and by rotating the support member 106 via a surgical tool inserted into the driver opening 185 so that the threaded portion 182 threadingly engages with the seat 152 and so that the flange 184 engages with the shoulder 155, or in any other desired manner. One or more endplates, such as the endplate 190 as will be described below, may be associated with the flanges 136 and/or 188, for example. In operation, the VBR apparatus 100 is configured to be implanted into a spine, and the support member 106 is configured to deflect when a force is applied to the VBR apparatus 100 by the adjacent vertebrae so that the VBR apparatus 100 is at least partially dynamic in an axial direction and/or in lateral direction when implanted into the spine and is in substantially constant contact with the adjacent vertebrae.

As will be appreciated by one of ordinary skill in the art, the VBR apparatus 100 may be coated with various compounds to increase bony on-growth or in-growth, promote healing, or allow for revision of the implant, including hydroxyapatite, titanium-nickel, vapor plasma spray deposition of titanium, or plasma treatment to make the surface hydrophilic, and combinations thereof, for example.

Figure 8:
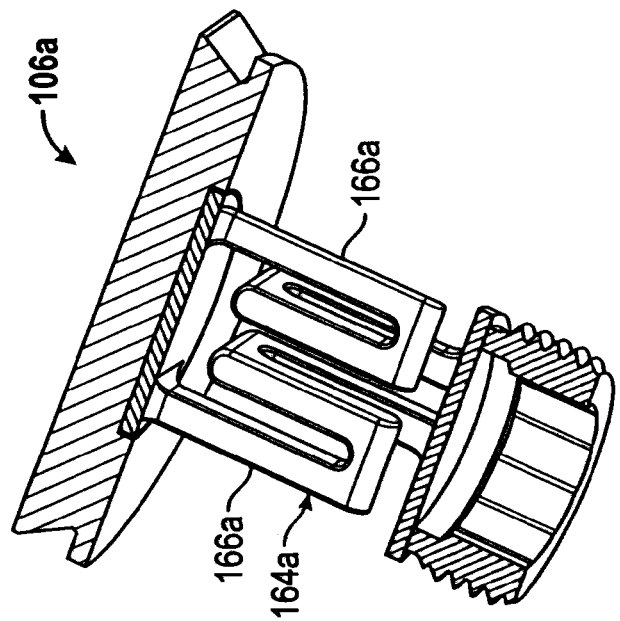
FIG. 8 is a cross-sectional view taken along line 8-8 of FIG. 7.
Figure 7:
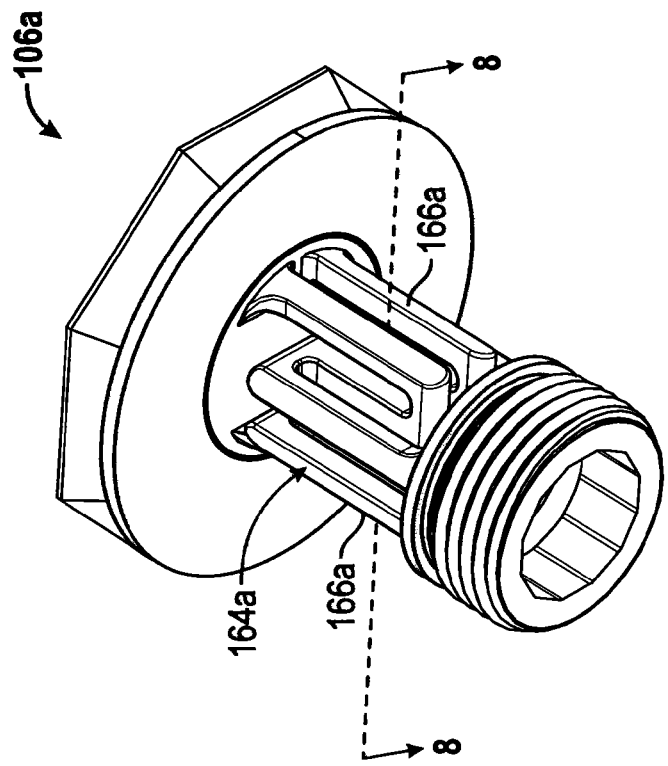
FIG. 7 is a perspective view of another embodiment of a support member.

Referring now to FIGS. 7-8, an exemplary embodiment of a support member 106a is shown therein. The support member 106a may be implemented and function similarly to the support member 106, and may be included in some exemplary embodiments of the VBR apparatus 100 where a lesser degree of flexibility or deflection of the VBR apparatus 100 is indicated. As will be appreciated by persons of ordinary skill in the art, the support member 106a has a spring portion 164a including shorter struts 166a than the struts 166 of the support member 106 and as such would be less elastic and/or would deflect axially and/or laterally to a lesser degree than a support member 106 assuming similarly sized gap 170. For example, the support member 106 may be implemented where the VBR apparatus 100 is used to replace a lumbar vertebral body, and the support member 106a may be implemented where the VBR apparatus 100 is used to replace a cervical or thoracic vertebral body. The spring portion 164a of the support member 106a may be implemented as any flexible element described in U.S. Pat. No. 8,252,059, for example, or as any other desired resilient or flexible member configured to deflect in an axial and/or in a lateral direction.

Figure 9:
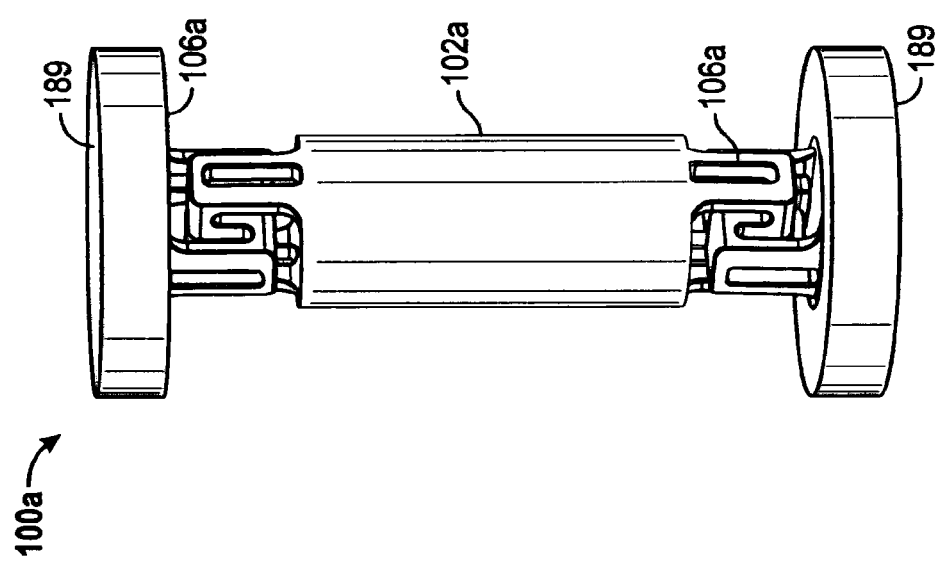
FIG. 9 is a perspective view of another embodiment of a VBR apparatus according to the inventive concepts disclosed herein.

Referring now to FIG. 9, another exemplary embodiment of a VBR apparatus 100a is shown therein as having a body member 102a, and a first support member 106a and a second support member 106a associated therewith.

The body member 102a may be substantially solid and may not be expandable in some exemplary embodiments. Further, in some exemplary embodiments, the body member 102a may have two or more body members movable relative to one another so as to expand the body member 102a and/or to adjust a height of the body member 102a. The first and second support members 106a may include ends 189 configured to matingly receive an endplate such as the endplate 190 thereon. Further, in some exemplary embodiments, the ends 189 of the first and second support members 106a may be configured as endplates (e.g., by having one or more bone-contacting surfaces) as will be appreciated by persons of ordinary skill in the art.

Figure 10:
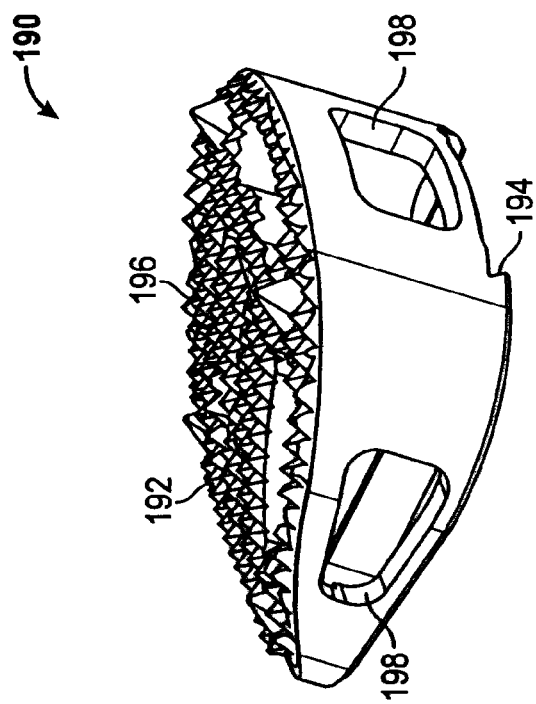
FIG. 10 is a perspective view of an exemplary embodiment of an endplate for a VBR apparatus according to the inventive concepts disclosed herein.

Referring now to FIG. 10, an exemplary embodiment of an endplate 190 that can be implemented with a VBR apparatus 100 or 100a according to the inventive concepts disclosed herein is shown.

The endplate 190 is configured to engage a vertebral body, and includes a bone-contacting surface 192 and an implant notch 194. The endplate 190 can be constructed of any desired bio-inert, bio-active, or bio-absorbable implantable material, or combination of materials, including titanium, titanium alloys, surgical steel, nickel titanium (or nitinol), cobalt chromium, polyether ether ketone (PEEK), plastics, metals, bone grafts (allografts or autographs), synthetic bone analogs, thermoplastic resins, alloys, non-metals, and plastics, for example. The endplate 190 may be manufactured by any suitable technique, such as molding, casting, machining, three-dimensional printing, etching, and combinations thereof, for example.

The bone-contacting surface 192 includes bone-contacting features 196, which may be implemented as ridges, grooves, bumps, spikes, protrusions, projections, striations, or combinations thereof, and are configured to securely retain the endplate 190 against a bone surface as the endplate 190 is implanted in the bone. The bone-contacting surface 192 can be coated with various compounds to increase or limit bony on-growth or in-growth, promote healing, long-term mobility, or allow for revision of the device, including hydroxyapatite, titanium-nickel, vapor plasma spray deposition of titanium, or plasma treatment to make the surface hydrophilic, and combinations thereof, for example. Also, a kit of endplates 190 having bone-contacting surfaces 192 with one or more varying sizes, shapes and angles may be provided.

The implant notch 194 may be configured to matingly receive the flange 136 and/or 188, and/or the first end 110 therein, so as to connect or otherwise associate the endplate 190 with a VBR apparatus 100 or 100a, for example.

The endplate 190 may include one or more openings 198 configured to promote bone graft fusion therein, as will be appreciated by persons of ordinary skill in the art, and may be constructed of any suitable material, such as titanium or PEEK, for example. Further, in some exemplary embodiments, the endplate 190 may be elastic and/or a variable angle endplate, such as the endplates described in PCT patent application Ser. No. PCT/US2012/65287.

As will be appreciated by persons of ordinary skill in the art, in some exemplary embodiments the endplate 190 may be omitted, and a bone-contacting surface such as the bone-contacting surface 192 may be provided on the flange 136 and/or on the flange 188. Further, in some exemplary embodiments, the flange 188 may be omitted, and an endplate 190 may be associated with the second end 162, for example.

Figure 11:
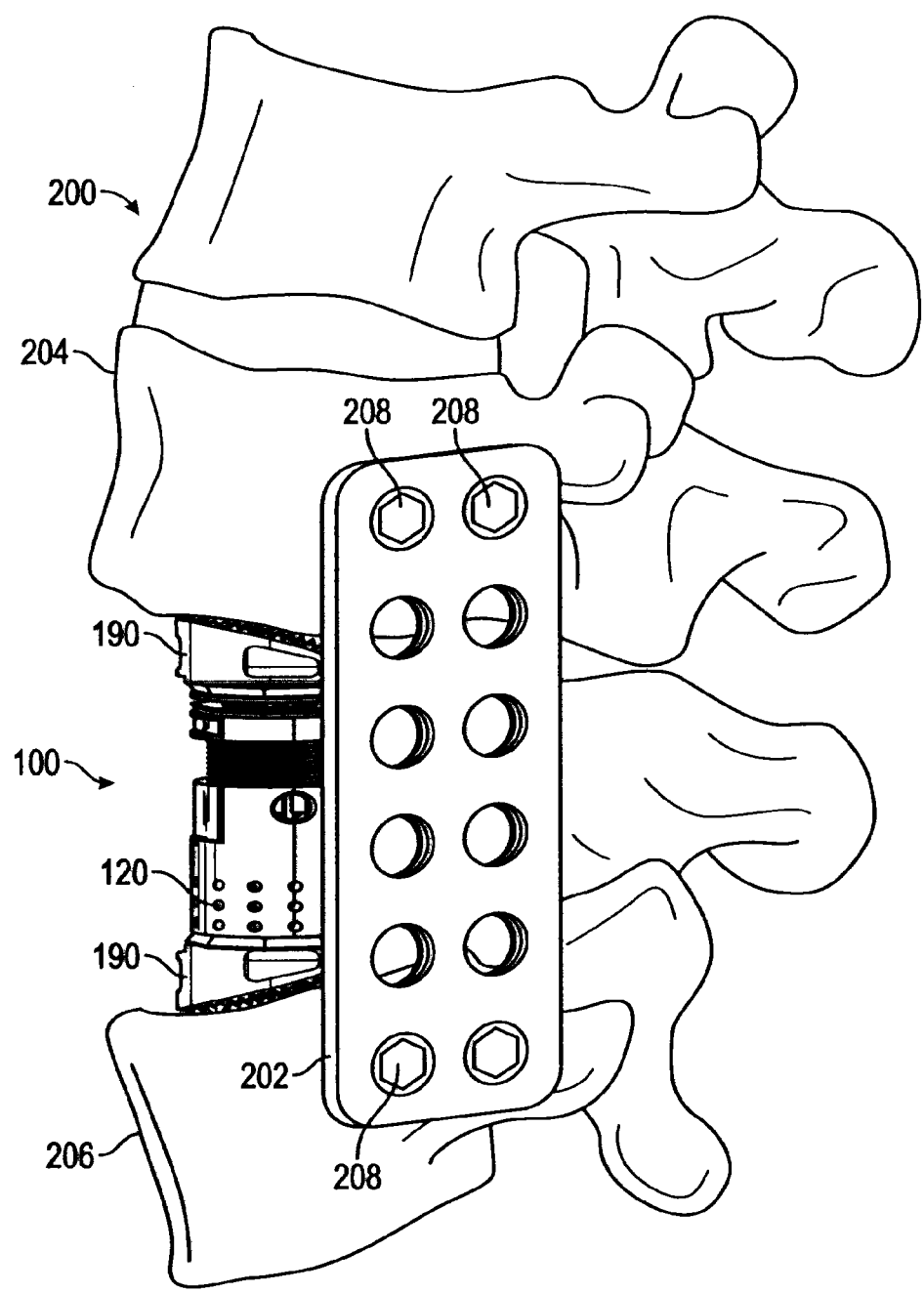
FIG. 11 is a diagram showing a VBR apparatus according to the inventive concepts disclosed herein shown implanted in a spine.

Referring now to FIG. 11, in operation a VBR apparatus 100 may be used as follows. A surgeon may select an appropriately sized VBR apparatus 100 from a kit of VBR apparatus 100 parts having various sizes, angles, dimensions, etc. The surgeon may select any desired size outer body member 102, inner body member 104, support member 106, and/or one or more endplate 190, according to the size of the patient's vertebral body being replaced and according to the space between adjacent vertebral bodies of the patient, for example. The surgeon may be provided with a kit including support members 106 with varying flexibility or degrees of deflection, and may select an appropriately sized support member 106 and/or inner body member 104 so as to achieve a desired degree of flexibility and/or deflection in the axial and/or lateral directions, by selecting appropriate components from the kit so as to adjust the height of the support member 106 and/or the size of the gap 170 between the sidewall 138 and the support member 106. For example, the larger the gap 170 and the larger the height of the support member 106, the more flexible the VBR apparatus 100 will be, and vice versa. In some embodiments, a kit of support member 106 and inner body member 104 pairs may be provided and may be identified by a respective degree of flexibility and/or deflection in axial and/or lateral directions to enable the surgeon to select an appropriate combination of a support member 106 and inner body member 104 depending on patient anatomy and spine angulation, for example.

If the VBR apparatus 100 is intended as a fusion VBR apparatus, the axial opening 118 of the outer body member 102 and/or the axial opening 148 of the inner body member 104 may be provided with a bone graft. If the VBR apparatus 100 is intended as a non-fusion VBR apparatus, no bone graft may be provided, for example.

The surgeon may associate the support member 106 with the inner body member 104, such as by inserting a suitable tool in the driver opening 185 of the support member 106 and rotating the support member 106 relative to the inner body member 104 so as to position the first end 160 of the support member 106 in the seat 152. The surgeon may slidably insert the inner body member 104 at least partially into the second end 112 of the outer body member 102 so that the locking member 124 engages the ratcheting teeth 130 of the inner body member 104. One or more endplates, such as the endplate 190 may be associated with the first end 110 of the outer body member 102 and with the second end 162 of the support member 106. The VBR apparatus 100 may be inserted into a desired location in a patient's spine 200 to replace a vertebral body. If desired, a bone graft may be provided in the VBR apparatus 100, prior to implanting the VBR apparatus 100 into the spine 200, or after implanting the VBR apparatus 100 into the spine 200.

A suitable surgical tool (not shown) may be used to expand the VBR apparatus 100 to adjust the height of the VBR apparatus 100 in an axial direction, such as by ratcheting or otherwise moving the inner body member 104 and the outer body member 102 relative to one another by grasping the notch 139 and the notch 143, for example. Once the VBR apparatus 100 is expanded so that the VBR apparatus 100 has the desired height, the surgeon may visually or physically verify that the locking member 124 is in the locked position to ensure that the desired height of the VBR apparatus 100 is maintained post-implantation.

A supplemental fixation device 202 such as a plate, may be implemented, and may be attached to adjacent vertebral bodies 204 and 206 and/or to the VBR apparatus 100, such as via one or more surgical screws 208 or by any other desired means, devices, or mechanisms, for example. The supplemental fixation device 202 can help stabilize the spine 200 and/or to retain the VBR apparatus 100 in place.

The correct position of the VBR apparatus 100 and/or the proper curvature of the spine 200 may be verified such as via suitable medical imaging, and the surgical incision may be closed.

After implantation, as forces are applied to the VBR apparatus 100 during normal movements of the patient's spine 200, the VBR apparatus 100 may remain slightly dynamic due to the operation of the support member 106 which deflects axially and/or laterally and/or rotationally. The degree of axial and/or lateral and/or rotational deflection of the VBR apparatus 100 may be determined by the length of the second end 162 (e.g., the length of the struts 166) and by the size of the gap 170, for example. In fusion systems, the VBR apparatus 100 remains slightly dynamic and transfers at least a portion of the applied forces to the bone graft provided therein so as to stimulate bone graft ingrowth and bone fusion. In non-fusion systems and/or in fusion systems the VBR apparatus 100 remains slightly dynamic and maintains substantially constant contact with the adjacent vertebral bodies 204 and 206, and transfers at least a portion of the applied forces to the supplemental fixation device 202 which minimizes point loading of the adjacent vertebral bodies 204 and 206 and/or substantially prevents subsidence of the adjacent vertebral bodies 204 and 206, for example. In some exemplary embodiments of the inventive concepts disclosed herein, VBR apparatuses such as the VBR apparatus 100 may promote micromotion or non-fusion as will be appreciated by persons of ordinary skill in the art.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed and as defined in the appended claims.

What is claimed is:

1. A vertebral body replacement apparatus, comprising:
   an outer body member having a first end, a second end, and an axial opening extending entirely through the outer body member from the first end to the second end, the first end configured to receive an endplate for engaging a first vertebral body;
   an inner body member having a first end, a second end, and an inner surface defining an axial opening extending entirely through the inner body member from the second end of the inner body member, the first end of the inner body member received in the axial opening of the outer body member such that the inner body member and the outer body member are movable relative to one another in a telescoping relationship such that the distance between the first end of the outer body member and the second end of the inner body member is selectively adjustable; and
   a support member having a first end and a second end, and a resilient portion between the first end and the second end, the second end of the support member configured to receive an endplate for engaging a second vertebral body, the support member positioned in the axial opening of the inner body member with the first end of the support member attached to the first end of the inner body member and the second end of the support member extending a distance beyond the second end of the inner body member, at least a part of the resilient portion of the support member positioned in the axial opening of the inner body member and separated from the inner surface of the inner body member by an uninterrupted annular gap about the resilient portion when the support member is in a substantially non-deflected condition so that the second end of the support member deflects relative to the first end of the outer body member in response to a force applied to the second end of the support member and returns to the substantially non-deflected condition upon release of the force,
   wherein an amount of deflection of the support member is based at least in part on the size of the annular gap.

2. The apparatus of claim 1, wherein the first end of the support member is detachably connected to the inner body member.

3. The apparatus of claim 2, wherein the first end of the support member is threadingly connected to the inner body member.

4. The apparatus of claim 3, wherein the first end of the support member has an axial opening configured to receive a driver for rotating the support member relative to the inner body member.

5. The apparatus of claim 2, wherein the inner surface of the inner body member has a shoulder and wherein the first end of the support member has a flange configured to engage the shoulder when the first end of the support member is secured within the inner body member.

6. The apparatus of claim 1, wherein the support member further has a spring portion positioned between the first end of the support member and the second end thereof, the spring portion spaced from the inner surface of the inner body member when the support member is in the non-deflected condition.

7. The apparatus of claim 6, wherein the spring portion is resilient in an axial direction.

8. The apparatus of claim 6, wherein the spring portion is resilient in a lateral direction.

9. The apparatus of claim 6, wherein the spring portion is resilient in an axial direction and a lateral direction.

10. The apparatus of claim 6, wherein the spring portion of the support member comprises:
    a first strut and a second strut extending from the first end of the support member in a substantially perpendicular direction thereto, the first strut and the second strut each having curved portions extending inwardly towards one another;
    a hanging beam positioned substantially parallel to the first strut and the second strut and connected to each of the curved portions of the first strut and the second strut; and
    a third strut and a fourth strut extending from the second end of the support member in a substantially perpendicular direction thereto, the third strut and the fourth strut each having a curved portion extending inwardly towards one another and connecting with a second end of the hanging beam.

11. The apparatus of claim 10, wherein the axial opening of the inner body member is substantially cylindrically shaped, and wherein the first strut, the second strut, the third strut, and the fourth strut define a substantially cylindrical shape.

12. A vertebral body replacement apparatus, comprising:
    an outer body member having a first end, a second end, and an axial opening extending from the first end to the second end;
    a first endplate connected to the first end of the outer body member for engaging a first vertebral body;
    an inner body member having a first end, a second end, and an inner surface defining an axial opening extending from the second end of the inner body member, the first end of the inner body member received in the axial opening of the outer body member such that the inner body member and the outer body member are movable relative to one another in a telescoping relationship such that the distance between the first end of the outer body member and the second end of the inner body member is selectively adjustable;
    a support member having a first end and a second end, and a resilient portion between the first end and the second end, the first end of the support member positioned in the axial opening of the inner body member with the first end of the support member threadingly connected to the first end of the inner body member and the second end of the supported member extending a distance beyond the second end of the inner body member, at least a part of the resilient portion of the support member positioned in the axial opening of the inner body member and separated from the inner surface of the inner body member by an uninterrupted annular gap about the resilient portion when the support member is in a substantially non-deflected condition such that the second end of the support member deflects relative to the first end thereof in response to a force applied to the second end and returns to the substantially non-deflected condition upon release of the force, wherein an amount of deflection of the support member is based at least in part on the size of the annular gap; and
    a second endplate connected to the second end of the support member for engaging a second vertebral body.

13. The apparatus of claim 12, wherein the first end of the support member is detachably connected to the inner body member.

14. The apparatus of claim 12, wherein the first end of the support member has an axial opening configured to receive a driver for rotating the support member relative to the inner body member.

15. The apparatus of claim 12, wherein the inner surface of the inner body member has a shoulder and wherein the first end of the support member has a flange configured to engage the shoulder when the first end of the support member is secured to the inner body member.

16. The apparatus of claim 12, wherein the support member further has a spring portion positioned between the first end of the support member and the second end thereof, the spring portion spaced from the inner surface of the inner body member when the support member is in a non-deflected condition.

17. The apparatus of claim 16, wherein the spring portion is resilient in an axial direction.

18. The apparatus of claim 16, wherein the spring portion is resilient in a lateral direction.

19. The apparatus of claim 16, wherein the spring portion is resilient in an axial and a lateral direction.

20. The apparatus of claim 16, wherein the spring portion of the support member comprises:
    a first strut and a second strut extending away from the first end of the support member in a substantially perpendicular direction thereto, the first strut and the second strut each having curved portions extending inwardly towards one another;
    a hanging beam positioned substantially parallel to the first strut and the second strut and connected to each of the curved portions of the first strut and the second strut; and
    a third strut and a fourth strut extending away from the second end of the support member in a substantially perpendicular direction thereto, the third strut and the fourth strut each having a curved portion extending inwardly towards one another and connecting with a second end of the hanging beam,
    wherein the first strut, the second strut, the third strut, and the fourth strut are spaced from the inner surface of the inner body member when the spring portion is in the non-deflected condition.

21. The apparatus of claim 20, wherein the axial opening of the inner body member is substantially cylindrically shaped, and wherein the first strut, the second strut, the third strut, and the fourth strut define a substantially cylindrical shape.

22. A vertebral body replacement apparatus, comprising:
    an outer body member having a first end, a second end, and an axial opening extending from the first end to the second end;
    a first endplate extending from the first end of the outer body member for engaging a first vertebral body;

an inner body member having a first end, a second end, and an inner surface defining an axial opening extending from the second end of the inner body member, the first end of the inner body member received in the axial opening of the outer body member such that the inner body member and the outer body member are movable relative to one another in a telescoping relationship such that the distance between the first end of the outer body member and the second end of the inner body member is selectively adjustable;

a support member having a first end and a second end, and a resilient portion between the first end and the second end, the support member positioned in the axial opening of the inner body member with the first end of the support member attached to the first end of the inner body member and the second end of the support member extending a distance beyond the second end of the inner body member, at least a part of the resilient portion of the support member positioned in the axial opening of the inner body member and separated from the inner surface of the inner body member by an uninterrupted annular gap about the resilient portion when the support member is in a substantially non-deflected condition such that the second end of the support member deflects relative to the first end thereof in response to a force applied to the second end and returns to the substantially non-deflected condition upon release of the force, wherein an amount of deflection of the support member is based at least in part on the size of the annular gap; and a second endplate extending from the second end of the support member for engaging a second vertebral body.

23. The apparatus of claim 22, wherein the inner surface of the inner body member has a shoulder and wherein the first end of the support member has a flange configured to engage the shoulder when the first end of the support member is secured to the inner body member, and wherein the support member is spaced apart from the inner surface of the inner body member from the shoulder to the second end of the support member when the support member is in the non-deflected condition.

24. The apparatus of claim 23, wherein the first end of the support member is threadingly connected to the inner body member.

* * * * *